(12) United States Patent
Schal et al.

(10) Patent No.: US 7,649,108 B2
(45) Date of Patent: Jan. 19, 2010

(54) PROCESS FOR THE DISTILLATION OF A MIXTURE OF ISOMERIC DIISOCYANATODIPHENYLMETHANES

(75) Inventors: Hans-Peter Schal, Dormagen (DE); Ulrich Wolf, Kerken (DE); Bernd Thelen, Leverkusen (DE)

(73) Assignee: Bayer MaterialScience AG, Leverkusen (DE)

( * ) Notice: Subject to any disclaimer, the term of this patent is extended or adjusted under 35 U.S.C. 154(b) by 451 days.

(21) Appl. No.: 10/838,456

(22) Filed: May 4, 2004

(65) Prior Publication Data
US 2004/0236139 A1 Nov. 25, 2004

(30) Foreign Application Priority Data
May 8, 2003 (DE) .................. 103 20 504
Jan. 14, 2004 (DE) ............... 10 2004 001 872

(51) Int. Cl.
*C07C 249/00* (2006.01)

(52) U.S. Cl. ............................. 560/352; 560/336
(58) Field of Classification Search ............. 560/352, 560/336; 558/420
See application file for complete search history.

(56) References Cited

U.S. PATENT DOCUMENTS

| 2,471,134 A | 5/1949 | Wright ................. 196/100 |
| 4,189,354 A | 2/1980 | Ellendt et al. ............ 203/81 |
| 4,294,666 A | 10/1981 | Astheimer et al. ........ 203/72 |
| 4,414,074 A | 11/1983 | Ellendt et al. ............ 203/21 |

FOREIGN PATENT DOCUMENTS

| GB | 1 417 087 | 12/1975 |
| GB | 1 423 993 | 2/1976 |

*Primary Examiner*—Taylor Victor Oh
(74) *Attorney, Agent, or Firm*—Lyndanne M. Whalen; Noland J. Cheung

(57) ABSTRACT

A mixture of isomeric diisocyanatodiphenylmethanes composed of at least 2,2'-diisocyanato-diphenylmethane, 2,4'-diisocyanatodiphenylmethane and 4,4'-diisocyanatodiphenylmethane is distilled in at least one stage and a divided-wall column is used in at least one distillation stage.

7 Claims, 3 Drawing Sheets

PROCESS FOR THE DISTILLATION OF A MIXTURE OF ISOMERIC DIISOCYANATODIPHENYLMETHANES

BACKGROUND OF THE INVENTION

The invention relates to a process for the distillation of a mixture including 2,2'-diisocyanatodiphenylmethane, 2,4'-diisocyanatodiphenyl-methane and 4,4'-diisocyanatodiphenylmethane in order to isolate 4,4'-diisocyanato-diphenyl-methane and mixtures of 4,4'- and 2,4'-diisocyanatodiphenylmethane containing little 2,2'-diisocyanatodiphenyl-methane.

Diisocyanatodiphenylmethane isomers are constituents of polyisocyanate mixtures of the diphenylmethane series, which occur on phosgenation of aniline/formaldehyde condensates, hereinafter also denoted polyaminopolyphenyl polymethanes.

The condensation of aniline and formaldehyde and the phosgenation of polyaminopolyphenyl polymethanes is known from the prior art. After the phosgenation of polyaminopolyphenyl polymethanes, phosgene is first completely removed. Then the higher homologues of diisocyanatodiphenylmethane (also denoted polyisocyanatopolyphenyl polymethanes) are separated. Pure 4,4'-diisocyanatodiphenylmethane is then separated from the remaining mixture of isomeric diisocyanatodiphenylmethanes, which mainly includes 2,2'-diisocyanatodiphenylmethane, 2,4'-diisocyanatodiphenyl-methane and 4,4'-diisocyanatodiphenylmethane. Various separation processes based on distillation or crystallization or a combination of distillation and crystallization are known in the prior art.

DE-A-2 322 574 may be mentioned as one example of the isolation of 4,4'-diisocyanatodiphenylmethane using a crystallization process. One disadvantage of the crystallization process is its elevated energy requirement because, especially if high purity 4,4'-diisocyanatodiphenylmethane is to be obtained, large quantities of refrigeration energy must be provided. DE-A-2 631 168 is an example of a distillation process for the separation of 4,4'-diisocyanatodiphenyl-methane. The process describes the multistage working up of a mixture of polyisocyanatopolyphenyl polymethanes to yield diisocyanatodiphenylmethane isomers. After separation by distillation of the more highly functional isocyanates, i.e. those having more than 2 isocyanate groups per molecule, the first distillation stream occurring in this stage, which substantially contains 2,2'-diisocyanatodiphenylmethane (hereinafter abbreviated to 2,2'-MDI), 2,4'-diisocyanatodiphenylmethane (hereinafter abbreviated to 2,4'-MDI) and 4,4'-diisocyanatodiphenylmethane (hereinafter abbreviated to 4,4'-MDI), is introduced into a first column and separated into a further distillation stream and a bottoms stream. The bottoms stream may amount to up to 10% by weight of the first distillation stream. The second distillation stream is fractionated in a second column into an overhead stream, which contains highly volatile impurities, 2,2'-diisocyanatodiphenylmethane and 2,4'-diisocyanato-diphenylmethane, and a bottoms stream, which predominantly contains fractions of 2,4'-MDI and 4,4'-diisocyanatodiphenylmethane. This bottoms stream is separated in a third column into 4,4'-MDI and a distillate fraction enriched with 2,4'-MDI. In the final distillation stage, 4,4'-MDI with a content of less than 2% by weight 2,4'-MDI is distilled off.

DE-A-2 933 601 and DE-A-3 145 010, for example, describe further processes for the isolation by distillation of 4,4'-diisocyanatodiphenylmethane or of mixtures of 4,4'- and 2,4'-diisocyanatodiphenylmethane. DE-A-3 145 010 proposes initially stripping out 2,2'- and 2,4'-diisocyanatodiphenylmethane as the overhead product from the diisocyanatodiphenylmethane isomer mixture, while 4,4'-MDI, from which isomers have largely been removed, is obtained as the bottoms product. In a final distillation, any polymerization products which have formed during the exposure to elevated temperatures should be removed from this bottoms product, while the overhead product is subjected to further working up by distillation.

In conventional distillation columns, the feed stream is conventionally divided into two product streams: an overhead product and a bottoms product. A multicomponent stream is thus not completely fractionated. Any further separations which are required may, for example, be performed by subjecting either the bottoms stream or the overhead stream to another distillation step similar to the first. Further distillation steps may optionally be performed thereafter. In continuous processes, it is necessary in such cases to provide each distillation step with its own column together with the associated evaporators and condensers. Such a sequence of distillation steps thus entails not only considerable expenditure on plant and equipment but also a considerable energy input. The operating costs of such a multistage distillation process are correspondingly high. Furthermore, in the case of MDI distillation, a substantial residue is formed by the exposure to elevated temperatures over two or more distillation stages, this residue consisting of secondary products such as for example uretidiones and carbodiimides, so reducing the quantity of target product.

SUMMARY OF THE INVENTION

The object of the present invention is to provide a process for the distillation of a mixture of isomeric diisocyanatodiphenylmethanes which includes 2,2'-diisocyanatodiphenylmethane, 2,4'-diisocyanatodiphenylmethane and 4,4'-diisocyanatodiphenylmethane, in which 4,4'-diisocyanatodiphenylmethane is obtained in elevated purity of at least 98% by weight. The intention is for the distillation process to require lower plant and equipment expenditure and a lower energy input than conventional distillation process for separating isomeric diisocyanatodiphenylmethanes.

These and other objects are accomplished by conducting at least one distillation of the isomeric mixture in a divided-wall distillation column.

DETAILED DESCRIPTION OF THE PREFERRED EMBODIMENTS OF THE INVENTION

Figure 1:
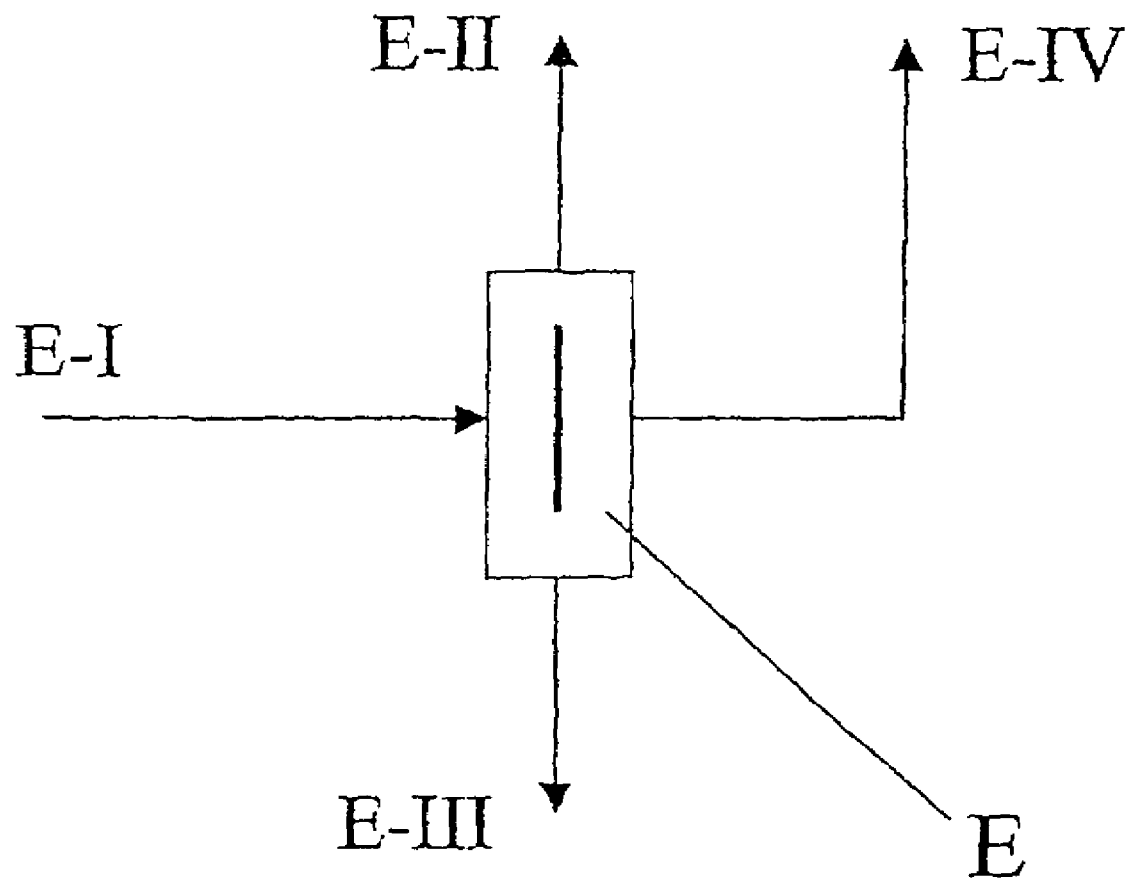
FIG. 1 is a diagram of a first embodiment of the process of the present invention with a divided-wall column.

The present invention provides a process for the distillation of a mixture of isomeric diisocyanatodiphenylmethanes that includes 2,2'-diisocyanatodiphenylmethane, 2,4'-diisocyanatodiphenylmethane and 4,4'-diisocyanatodiphenylmethane, in which the distillation is performed in at least one stage and a divided-wall column is used in at least one distillation stage.

U.S. Pat. No. 2,471,134, for example, discloses the distillation of a multi-component mixture in a divided-wall column. In a divided-wall column, a partition runs vertically in the central part of the column. In this manner, the column is divided into four zones: a pre-fractionation zone and a main fractionation zone in the region of the partition, together with a bottoms zone (exhausting zone) and a rectification zone (overhead zone). The multi-component stream is fed into the pre-fractionation zone. The overhead product is drawn off from the rectification zone, the bottoms product from the exhausting zone. An intermediate product is drawn off from the main fractionation zone.

Diisocyanatodiphenylmethane mixtures (hereinafter also called starting mixtures) with the most varied proportions of 2,2'-diisocyanatodiphenylmethane, 2,4'-diisocyanatodiphenylmethane and 4,4'-diisocyanatodiphenylmethane can be distilled using the process according to the invention. In the starting mixture, the proportions of 4,4'-MDI are preferably from 35 to 95% by weight, the total of 2,2'-MDI and 2,4'-MDI preferably amounting to 5 to 65% by weight. The proportion of 2,2'-MDI preferably amounts to 1 to 10% by weight, relative to 2,4'-MDI.

Preferred starting mixtures are those comprising at most 3.0% by weight 2,2'-diisocyanatodiphenylmethane, 5 to 50% by weight 2,4'-diisocyanatodiphenylmethane and 50 to 95% by weight 4,4'-diisocyanatodiphenylmethane. Mixtures composed of 5-25% by weight 2,4'-MDI and 75-95% by weight 4,4'-MDI are particularly preferred.

The starting mixture may further contain: chlorobenzene and other lower-boiling compounds, for example phenyl isocyanate, with a content of less than 2% by weight, 0 to 5% by weight polyisocyanatopolyphenylmethanes and 0 to 5% by weight higher molecular weight compounds which have been formed by exposure to elevated temperatures.

Such a mixture of isomeric diisocyanatodiphenylmethanes occurs on phosgenation of polyaminopolyphenyl polymethanes, which are produced by condensation of aniline and formaldehyde, to yield polyisocyanatopolyphenyl polymethanes. After the phosgenation, which is preferably performed in monochlorobenzene (MCB) as the solvent, the solvent and phosgene are first of all completely removed by distillation methods. Then, by means of distillation in a polymer separation operation known per se (See, for example, DE 2631168), a mixture of polyisocyanatopolyphenyl polymethanes and diisocyanatodiphenylmethanes, on the one hand, and a mixture of the three isomers 2,2'-diisocyanatodiphenylmethane, 2,4'-diisocyanatodiphenylmethane and 4,4'-diisocyanatodiphenylmethane together with solvent residues and other low-boiling substances such as phenyl isocyanate, on the other, are obtained. The latter mixture serves as the starting mixture for the process according to the present invention.

The starting mixture of isomeric diisocyanatodiphenylmethanes is introduced into the side of the divided-wall column in the region of the partition.

The divided-wall column is located in the central zone of the column. The length of the partition depends on the process conditions and on the properties of the material exchange members used. When a woven fabric packing with a specific surface area of for example 500 m$^2$/m$^3$ is used, the length of the partition is approx. 8 m, i.e. 2/3 of the entire material exchange zone is within the region of the partition. The partition divides the column into a pre-fractionation zone and a main fractionation zone.

Vapor flow in the pre-fractionation zone and the main fractionation zone is established in accordance with packing pressure losses. The total pressure at the inlet and outlet regions of the partition is identical for both zones. Should it be desired for processing reasons to expose one zone within the region of the partition more strongly to vapor, different cross-sections of the pre-fractionation zone and main fractionation zone may also be selected. The process may be optimized by appropriate selection of the partial cross-sections of the two zones.

Packings are particularly suitable as material exchange members. It is, however, possible to use other members known in distillation technology, such as packing shapes or trays.

With regard to pressure and temperature, the divided-wall column is operated under similar process conditions to a conventional distillation column. Overhead pressure is preferably in the range from 3 to 12 mbar. Depending on mixture composition, the overhead temperature is preferably 165 to 200° C. Bottoms pressure is preferably 11 to 20 mbar at preferred temperatures of 210 to 225° C.

When the mixture of isomeric diisocyanatodiphenylmethanes is distilled in the divided-wall column, the bottoms product obtained is 4,4'-diisocyanatodiphenylmethane with an isomeric purity (i.e., a purity relative to the three isomers 2,2'-MDI, 2,4'-MDI and 4,4'-MDI) of at least 98% by weight.

When the mixture of isomeric diisocyanatodiphenylmethanes is subjected to single-stage distillation in the divided-wall column, the bottoms product preferably obtained is 4,4'-diisocyanatodiphenylmethane with a purity of at least 98% by weight, the overhead product obtained, depending on the feed stream, is a mixture composed of at most 60% by weight 2,2'-diisocyanatodiphenylmethane, 40 to 80% by weight 2,4'-diisocyanatodiphenylmethane and up to 5% by weight 4,4'-diisocyanatodiphenylmethane, and the side stream obtained is a mixture of 2,4'-diisocyanatodiphenylmethane and 4,4'-diisocyanatodiphenylmethane in a ratio by weight of 85:15 to 15:85.

The divided-wall section is particularly preferably configured such that an MDI mixture of 50 to 60% by weight 2,4'-MDI and 40 to 50% by weight 4,4'-MDI is drawn off in the side stream. The concentration of 2,4'-MDI in the side stream can be adjusted within broad limits from 15 to 85% by weight by suitable division of fluids between the partition and the rectification zone.

The overhead reflux ratio is in particular adjusted to within a range from 10 to 250, but is particularly preferably in a range from 60 to 120, wherein the distillate stream amounts to 1-5% by weight relative to the feed stream. The bottoms stream amounts to 60 to 90% by weight, preferably 75 to 85% by weight, of the feed stream.

Alternatively, the distillation process according to the invention may also be performed in two stages, wherein the first distillation stage is performed in a distillation column without a partition, the second stage with a divided-wall column. The overhead product from the first distillation stage is supplied to the divided-wall column of the second stage.

In the two-stage process, the second distillation stage with the divided-wall column is performed under conditions comparable to those used in the single-stage process. With regard to pressure and temperature, the divided-wall column is operated under similar process conditions to a conventional distillation column. Overhead pressure is in the range from 3 to 12 mbar. Depending on the composition of the mixture, the overhead temperature is 165 to 200° C. Bottoms pressure is in the range from 11 to 20 mbar at temperatures of 210 to 225° C. The divided-wall section is preferably configured such that an MDI mixture of 50 to 60% by weight 2,4'-MDI and 40 to 50% by weight 4,4'-MDI may be drawn off in the side stream. The concentration of 2,4'-MDI in the side stream can be adjusted within broad limits from 15 to 85% by weight by suitable division of fluids between the partition and the rectification zone. The overhead reflux ratio is preferably adjusted to within a range from 5 to 80, but is particularly preferably in a range from 10 to 40, wherein the distillate stream amounts to 5-20% by weight relative to the feed stream. The bottoms stream preferably amounts to 7 to 30% by weight, particularly preferably 15 to 25% by weight, of the feed stream.

In order to achieve still higher purity of the 4,4'-MDI, in a preferred embodiment of the process according to the invention, after the distillation in the divided-wall column, the bottoms product from the divided-wall column is additionally distilled in a distillation column without a partition. This additional distillation to achieve higher purity may be used both in the single-stage process with a divided-wall column and in the two-stage process with a first distillation column without a partition and a second distillation column with a partition.

In another embodiment of the present invention, the distillation of the mixture of isomeric diisocyanatodiphenylmethanes is performed in two stages with a divided-wall column in each distillation stage. The overhead product from the first divided-wall column is supplied to the second divided-wall column. The combination of two divided-wall columns makes it possible to dispense with the purification stage in a conventional distillation column which is otherwise usually performed after the distillation, as described above, in order to achieve particularly high purity.

Preferably at least 98% by weight, more preferably 98.5 to 99.0% by weight commercially usable 4,4'-MDI is drawn off as a side stream from the first divided-wall column. The overhead product from the first column contains substantially all of the introduced 2,2'-MDI and is composed of an isomer mixture of 2,2'-MDI (preferably 0.5 to 5.0% by weight), 2,4'-MDI (29.0 to 55.0% by weight) and 4,4'-MDI (40.0 to 70.0% by weight). It also contains the low-boiling components, such as for example chlorobenzene, introduced with the feed. The bottoms predominantly contain 4,4'-MDI (99.5 to 99.95% by weight) with higher molecular weight secondary products as impurities which have occurred due to exposure to elevated temperatures, and less than 0.5% by weight 2,4' MDI.

With regard to pressure and temperature, the first divided-wall column is operated under similar process conditions to a conventional distillation column. Overhead pressure is preferably in the range from 3 to 12 mbar. Depending on mixture composition, the overhead temperature is preferably 165 to 200° C. Bottoms pressure is preferably between 11 and 20 mbar at temperatures of 210 to 225° C. 50-80% by weight of the liquid discharged from the rectification zone is introduced into the pre-fractionation zone. The remaining 20-50% by weight are directed into the main fractionation zone. 40-80% by weight are drawn off as a product stream in the side stream.

The second divided-wall column in this embodiment of the process according to the invention is operated under conditions comparable to those prevailing in the divided-wall column of the second stage in the above-described two-stage process with a conventional distillation column in the first distillation stage. The composition of the overhead stream of this second divided-wall column substantially corresponds to the composition of the overhead stream of the divided-wall column in the one-stage process, i.e. at most 60% by weight 2,2' MDI, 40 to 80% by weight 2,4' MDI and a maximum of 5% by weight 4,4' MDI. The side stream contains at most 0.2% by weight 2,2' MDI, 50 to 60% by weight 2,4' MDI and 40 to 50% by weight 4,4' MDI. The bottoms stream is substantially free of 2,2'-MDI. The concentration of 2,4'-MDI can be up to 25% by weight, but is preferably less than 2% by weight. This product can therefore also be used commercially.

The use of at least one divided-wall column in order to isolate 4,4'-MDI in high (at least 98% by weight) or very high purity (at least 99% by weight) from a mixture of three isomeric diisocyanatodiphenylmethanes makes it possible to save one or two distillation stages in comparison with prior art distillation processes. On the one hand, plant and equipment expenditure is consequently considerably lower because it is possible to dispense not only with the distillation column but also with additional heat exchangers, piping, etc. On the other hand, energy input is significantly reduced as a consequence, as less heat need be supplied. Furthermore, the smaller number of distillation stages and the consequently reduced exposure to elevated temperatures mean that there is a smaller proportion of residues resulting from isocyanate group reactions.

The invention is illustrated in greater detail below with reference to the drawings and the Examples.

In the figures, identical or similar distillation columns and streams are denoted with identical reference symbols.

EXAMPLES

Example 1

A single-stage distillation was performed with a divided-wall column of the type shown in FIG. 1. 5.9 kg/h of an isomer mixture composed of 0.6% by weight 2,2'-MDI, 11.1% by weight 2,4'-MDI and 88.3% by weight 4,4'-MDI (stream E-I) were introduced into the divided-wall column E in the region of the partition. Three product streams were drawn off from the divided-wall column: 0.15 kg/h of overhead stream E-II composed of 23.5% by weight 2,2'-MDI, 75.0% by weight 2,4'-MDI and 1.5% by weight 4,4'-MDI and 0.95 kg/h of side stream E-IV composed of 0.05% by weight 2,2'-MDI, 54.90% by weight 2,4'-MDI, 44.05% by weight 4,4'-MDI and 4.8 kg/h of bottoms stream E-III with an isomeric purity of 4,4'-MDI of 99%. The purity of the 4,4'-MDI could be increased by transferring the bottoms stream E-III into an additional distillation column without a partition.

The material exchange members used in the divided-wall column were woven fabric packings with a specific surface area of 500 m$^2$/m$^3$. 67% by weight of the liquid were directed into the pre-fractionation zone and 33% by weight into the main fractionation zone. The rectification zone and the exhausting zone each had 8 separation stages, the pre-fractionation zone and the main fractionation zone each had 12 separation stages above and below (i.e., the separation stages above and below the feed inlet of the feed stream into the pre-fractionation zone or the side stream discharge point from the main fractionation zone). Overhead pressure was 6 mbar. Reflux at the distillate discharge point was 90:1, while reflux at the side stream discharge point was 2.6:1.

Example 2

Figure 2:
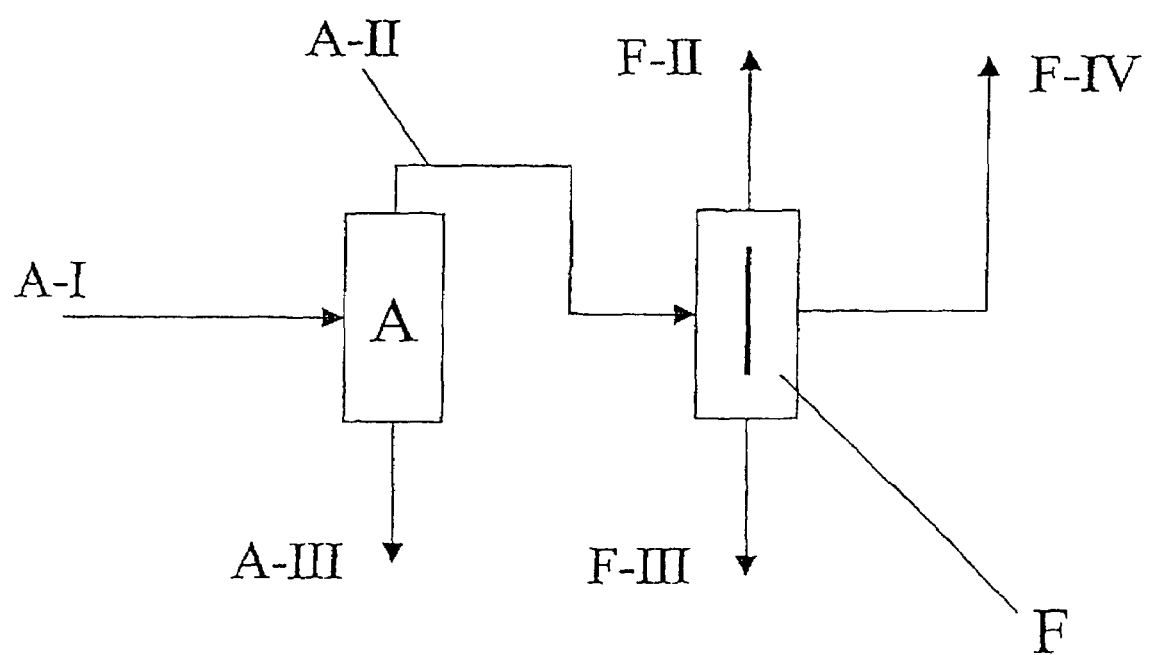
FIG. 2 is a diagram of a second embodiment of the process of the present invention in which a conventional distillation column is used in the first stage and a divided-wall column is used in the second stage.

A two-stage distillation was performed with a conventional distillation column A in stage 1 and a divided-wall column F in stage 2 as illustrated in FIG. 2. With reference to FIG. 2, 6.3 kg/h of an isomer mixture composed of 2,2'-MDI (0.6% by weight), 2,4'-MDI (11.1% by weight) and 4,4'-MDI (88.3% by weight) were supplied to the rectification column A (stream A-I). 1.55 kg/h of mixture composed of 2.3% by weight 2,2'-MDI, 42.0% by weight 2,4'-MDI and 55,7% by weight 4,4'-MDI were drawn off at the top of the rectification column A (stream A-II). The bottoms product from column A (stream A-III, 4.8 kg/h) contained 4,4'-MDI of elevated purity (97% by weight). The overhead pressure in column A was 6 mbar. Reflux at the distillate discharge point was 6.5:1. The rectification zone had 8 separation stages, while the exhausting zone had 18 separation stages.

Overhead stream A-II was fed into the divided-wall column F. On distillation, 0.15 kg/h of an overhead stream composed of 24.5% by weight 2,2'-MDI, 75.3% by weight 2,4'-MDI and 0.2% by weight 4,4'-MDI were drawn off (stream F-II). 4,4'-MDI with an isomeric purity of 99% (0.4 kg/h) was drawn off at the bottom of the column (stream F-III). The side stream F-IV, which was drawn off from the lower quarter of the partition zone, was composed of less than 0.1% by weight 2,2'-MDI, 55% by weight 2,4'-MDI and 45% by weight 4,4'-MDI. The overhead pressure in the divided-wall column F was 6 mbar. Reflux at the distillate discharge point was 21:1, while it was 1.4:1 at the side stream discharge point. The rectification zone and the bottoms zone each had 8 separation stages. The pre-fractionation zone had 8 separation stages above and 20 separation stages below. The main fractionation zone had 22 separation stages above and 6 separation stages below. The material exchange members used in the divided-wall column F were woven fabric packings with a specific surface area of 500 m²/m³. 67% by weight of the liquid were directed into the pre-fractionation zone and 33% by weight into the main fractionation zone.

In order to achieve higher purity of 4,4'-MDI, streams A-III and/or F-III could be transferred into an additional distillation column without a partition, for example, for flash distillation.

Example 3

A single-stage distillation was performed with a divided-wall column E as illustrated in FIG. 1. 6.33 kg/h of an isomer mixture composed of 0.6% by weight 2,2'-MDI, 10.8% by weight 2,4'-MDI, 87.9% by weight 4,4'-MDI and 0.7% by weight higher boiling impurities were supplied to the divided-wall column E (feed stream E-I). The bottoms stream E-III was 0.4 kg/h and was composed of 99% by weight 4,4'-MDI and 1% by weight impurities. The overhead stream E-II was an isomer mixture composed of 2.4% by weight 2,2'-MDI, 41.0% by weight 2,4'-MDI and 56.6% by weight 4,4'-MDI. The purity of 4,4'-MDI, which was drawn off as a side stream E-IV at a rate of 4.37 kg/h, was 98.9% by weight.

The material exchange members used in the divided-wall column E were woven fabric packings with a specific surface area of 500 m²/m³. 67% by weight of the liquid was directed into the pre-fractionation zone and 33% by weight into the main fractionation zone. Overhead pressure was 6 mbar. Reflux at the distillate discharge point was 6.5:1, reflux at the side stream discharge point was 1.8:1. The rectification zone had 8 separation stages, the exhausting zone at most 4 separation stages. The pre-fractionation zone had 8 separation stages above and 16 separation stages below. The main fractionation zone had 16 separation stages above and 8 separation stages below.

The overhead stream E-II (FIG. 1) could be introduced for further working up either into a conventional distillation column or into a divided-wall column, the bottoms stream of which containing a small proportion of 2,2'-MDI may in turn be introduced into a further conventional distillation column. Pure 4,4'-MDI was obtained at the bottom of this second conventional distillation column, while the overhead stream yielded a 2,4'-MDI-rich product.

Example 4

Figure 3:
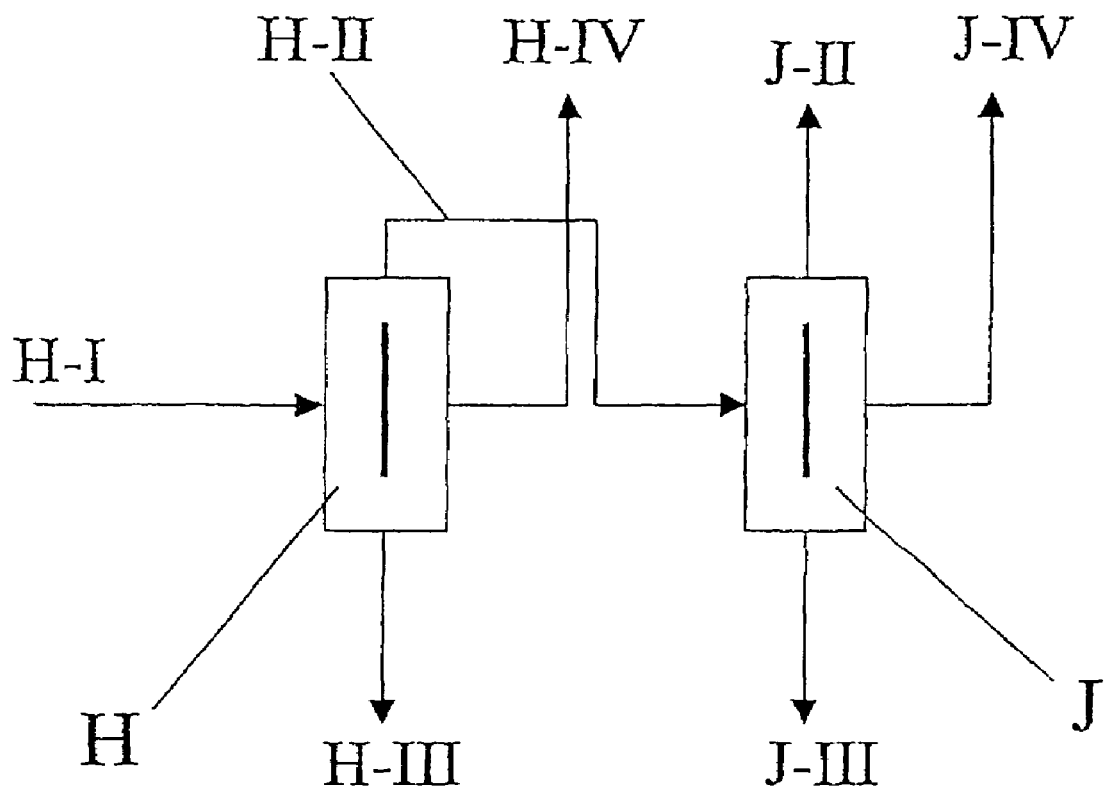
FIG. 3 is a diagram of another embodiment of the present invention in which a divided-wall distillation column is used in each of two distillation stages.

A two-stage distillation was performed with two divided-wall columns H and J as illustrated in FIG. 3. The isomer mixture with a composition of 0.5% by weight 2,2'-MDI, 11.1% by weight 2,4'-MDI and 88.4% by weight 4,4'-MDI was introduced into the first column H in the region of the partition (stream H-I, 6.33 kg/h). A highly enriched 4,4'-MDI (isomeric purity 99%) with impurities was obtained as the bottoms product H-III (0.4 kg/h). The content of 4,4'-MDI in the side stream discharge H-IV (4.38 kg/h) was 98.8% by weight. 77% by weight of the introduced 4,4'-MDI were discharged with H-IV.

The material exchange members used in the divided-wall column H were woven fabric packings with a specific surface area of 500 m²/m³. 67% by weight of the liquid was directed into the pre-fractionation zone and 33% by weight into the main fractionation zone. Overhead pressure was 6 mbar. Reflux at the distillate discharge point was 6.5:1, reflux at the side stream discharge point was 1.8:1. The rectification zone had 8 separation stages, the exhausting zone at most 4 separation stages. The pre-fractionation zone had 8 separation stages above and 16 separation stages below. The main fractionation zone had 16 separation stages above and 8 separation stages below.

The overhead product H-II was an isomer mixture enriched with isocyanate groups in ortho position, which needed to be further separated in order to produce 2,4'-MDI-rich products. The overhead product H-II from the first column H was thus introduced into the second divided-wall column J in the region of the partition.

The bottoms product J-III from column J was 4,4'-MDI (0.43 kg/h) from which 2,2'-MDI had been removed and contained 1% by weight 2,4'-MDI, relative to the isomer content. The side stream J-IV had a composition of 0.05% by weight 2,2'-MDI, 55% by weight 2,4'-MDI and 45% by weight 4,4'-MDI. The 2,2'-MDI was discharged from the system with the overhead product (stream J-II, 0.15 kg/h) of the composition 23.5% by weight 2,2'-MDI, 75% by weight 2,4'-MDI and 1.5% by weight 4,4'-MDI.

The overhead pressure in the divided-wall column J was 6 mbar. Reflux at the distillate discharge point was 21:1, while it was 1.4:1 at the side stream discharge point. The rectification zone and the bottoms zone each had 8 separation stages. The pre-fractionation zone had 8 separation stages above and 20 separation stages below. The main fractionation zone had 22 separation stages above and 6 separation stages below. The material exchange members used in the divided-wall column J were woven fabric packings with a specific surface area of 500 m²/m³. 67% by weight of the liquid were directed into the pre-fractionation zone and 33% by weight into the main fractionation zone.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the distillation of a mixture of isomeric diisocyanatodiphenylmethanes said mixture comprising 2,2'-diisocyanatodiphenyl-methane, 2,4'-diisocyanatodiphenyl-methane and 4,4'-diisocyanato-diphenylmethane in which the distillation is performed in at least one stage using a divided-wall column wherein (a) a bottoms product of 4,4'-diisocyanatodiphenyl-methane having a purity of at least 98% by weight is obtained in the divided wall column and (b) a mixture of
  (i) 50-60% by weight of 2,4'-diisocyanatodiphenyl-methane
  and
  (ii) 40-50% by weight of 4,4'-diisocyanatodiphenyl-methane is drawn off in a side stream in the divided wail column.

2. The process of claim 1 in which the mixture of isomeric diisocyanatodiphenylmethanes being distilled comprises 75 to 95% by weight 4,4'-diisocyanatodiphenylmethane.

3. The process of claim 1 in which the distillation is performed in two stages with a divided-wall column in the second distillation stage.

4. The process of claim 3 in which overhead product from the first distillation stage is introduced into the divided-wall column of the second distillation stage.

5. The process of claim 1 comprising subjecting bottoms product from the divided-wall column to further distillation.

6. The process of claim 1 in which the distillation is performed in two stages and a divided-wall column is used in each distillation stage.

7. The process of claim 6 in which overhead product from the first divided-wall column is introduced into the second divided-wall column.

* * * * *